United States Patent [19]

Campbell

[11] Patent Number: 4,642,894
[45] Date of Patent: Feb. 17, 1987

[54] HOME CARE DENTURE GRINDING INSTRUMENT

[75] Inventor: Bruce T. Campbell, Lakewood, Calif.

[73] Assignee: Camdent Laboratories, Cerritos, Calif.

[21] Appl. No.: 733,086

[22] Filed: May 13, 1985

Related U.S. Application Data

[62] Division of Ser. No. 511,190, Jul. 6, 1983, Pat. No. 4,530,259.

[51] Int. Cl.⁴ .......................... B26B 3/00; A61C 3/00
[52] U.S. Cl. ..................................... 30/169; 30/340; 15/236 R; 433/143
[58] Field of Search ............... 15/236 R; 30/169, 168, 30/294, 340, 314, 286; 433/144, 141, 145; 76/101 R; 128/303

[56] References Cited

U.S. PATENT DOCUMENTS

| | | | |
|---|---|---|---|
| 423,351 | 3/1890 | Streeter | 30/340 X |
| 1,547,829 | 7/1925 | Shoffner | 30/168 |
| 2,280,007 | 4/1942 | Plateck | 30/168 |
| 2,558,242 | 6/1951 | Ernst | 30/168 |
| 2,677,843 | 5/1954 | Goodman | 15/236 R |
| 3,267,506 | 8/1966 | Van Patten | 15/236 R |
| 3,460,256 | 8/1969 | Fontana | 433/144 |
| 3,504,440 | 4/1970 | Fontana | 433/144 |
| 4,062,117 | 12/1977 | Coleman | 30/294 X |
| 4,140,123 | 2/1979 | Curutchet | 30/340 |
| 4,270,902 | 6/1981 | Wiland | 433/144 |
| 4,274,826 | 6/1981 | Huey | 30/294 |
| 4,377,381 | 3/1983 | Westman | 433/144 |
| 4,530,259 | 7/1985 | Campbell | 30/169 X |
| 4,565,004 | 1/1986 | Heinz | 30/314 |

Primary Examiner—Jimmy C. Peters
Attorney, Agent, or Firm—Leonard Tachner

[57] ABSTRACT

A grinding instrument, especially adapted to permit wearer adjustment of dentures, comprises an S-shaped handle, a straight shaft and a blade, the handle, shaft and blade all being integral sequential members of a unitary, elongated cylindrical wire. In a preferred embodiment the wire is made of a seven and one-half inch length of four millimeter diameter carbon steel wire in a novel process comprising the steps of:

cutting a carbon steel wire to a selected straight length,
bending about one-half of said length of wire to form a handle,
stamping the terminal portion of the unbent half of said length of wire to form a shaft terminating in a blade, and
grinding at least one surface of said blade at a selected angle relative to the longitudinal axis of said shaft to form a grinding edge.

1 Claim, 7 Drawing Figures

U.S. Patent     Feb. 17, 1987     4,642,894
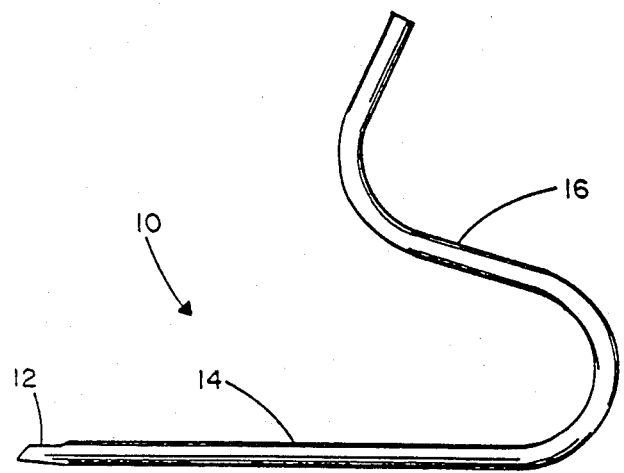
FIG. 1
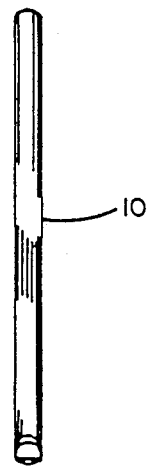
FIG. 2
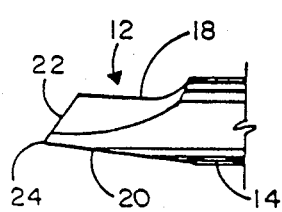
FIG. 3
FIG. 4
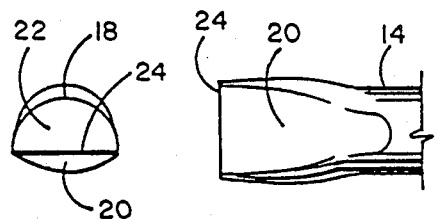
FIG. 5
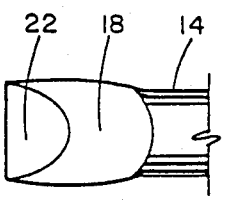
FIG. 6
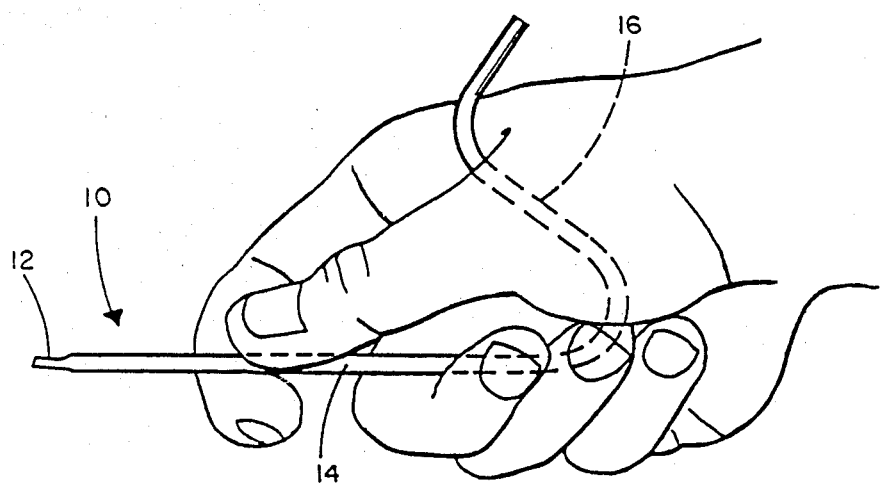
FIG. 7

HOME CARE DENTURE GRINDING INSTRUMENT

This is a division of Application Ser. No. 511,190 filed July 6, 1983 and now U.S. Pat. No. 4,530,259 issued July 23, 1985.

BACKGROUND OF THE INVENTION

1. Field of the Invention

The present invention relates to dental implements and more particularly, to a denture grinding instrument which may be used by the wearer on an emergency basis to grind away a part of a denture which is causing pain.

2. Prior Art

It is well-known, particularly by the wearers of dentures, that it is often necessary to adjust the fit of dentures to the gums. Of course, the vast majority of denture wearers do not have the skill or training required to properly adjust their dentures for changing gum conditions. Accordingly, it is always best for a denture wearer in need of adjustment to his or her dentures to return to the dentist's office to permit the expert to make any required adjustments. However, it is not always convenient to do so immediately upon the need arising. As a result, it is often necessary for denture wearers to experience a great deal of pain caused by their dentures or to forego the use of their dentures entirely until they have an opportunity to have an adjustment made by the expert.

The present invention consists of a home care denture grinding instrument that comprises part of an emergency denture adjustment kit. Thus the present invention, particularly when used with the aforementioned kit, provides denture wearers the opportunity to adjust their dentures under emergency conditions on an interim basis before they have the opportunity to have their dentures adjusted professionally. There are a number of prior art denture-related tools which proport to give the wearer the opportunity to make such adjustments. By way of example, the applicant is aware of the following four relevant patents:

U.S. Pat. No. 3,460,256, Fontana
U.S. Pat. No. 3,504,440, Fontana
U.S. Pat. No. 4,274,826, Huey et al
U.S. Pat. No. 4,377,381, Westman Irrespective of efficacy of each tool for the purpose intended, the relative disadvantage of each such tool with respect to the present invention is that each requires a fairly complex and costly manufacturing process which renders each such tool virtually as expensive as any specialized denture tool would normally be and such expense defeats the very purpose for which the tools are intended. As a result, many denture wearers tend to make emergency denture adjustments using a variety of tools which are not proper for the work to be done, such as nail files, screwdrivers, table knives and the like.

More specifically, each of the aforementioned tools includes one or more specially designed tips made integral with a special handle particularly designed for that tool. The comparative size, shape and structure of the prior art tools are therefore factors which not only increase the cost to the ultimate consumer, but which also affect the packaging requirements for the sale of the kits. Such packaging requirements also tend to increase the cost which denture wearers have to pay to possess a handy means for adjusting their dentures in emergency situations.

SUMMARY OF THE INVENTION

The present invention comprises a home care denture grinding instrument for emergency use by denture wearers and substantially reduces or entirely overcomes the aforementioned disadvantages of the prior art. More specifically, the present invention is a denture grinding tool which is of unique shape and capable of uniquely simple manufacture to provide an instrument which clearly meets the denture adjustment capabilities of wearers. This unique tool is of sufficiently low cost and easily packaged to provide an advantageous adjunct to a kit which can be used by denture wearers to make emergency adjustments to their dentures. The tool of the present invention comprises an S-shaped cylindrical wire with a blade, shaft and handle, all integral thereto. In the preferred embodiment of the invention, this wire is approximately 4 millimeters in diameter and because its shape alone provides the user with a necessary gripping means, no special tool assembly is required during the manufacturing process. The packaging of the tool, with or without the remainder of the kit with which it is normally sold, may take advantage of its uniquely small dimensions.

OBJECTS OF THE INVENTION

It is therefore a principal object of the present invention to provide a grinding instrument useful for emergency adjustment of dentures by their wearers and which substantially reduces or entirely overcomes the aforementioned disadvantages of the prior art.

It is an additional object of the present invention to provide a grinding instrument which is of unique simple structure and of minimum dimension to enable low-cost manufacture and packaging and thereby discourage the use of improper and potentially injurious tools which denture wearers might otherwise tend to use for such purposes.

It is still an additional object of the present invention to provide a denture grinding instrument which is manufactured from a unitary length of wire which is shaped to provide the user with a handle without requiring any costly and time consuming assembly during the manufacturing process.

BRIEF DESCRIPTION OF THE DRAWINGS

The aforementioned objects and advantages of the present invention as well as additional objects and advantages thereof will be more fully understood hereinafter as a result of a detailed description of a preferred embodiment of the invention when taken in conjunction with the accompanying drawings in which:

FIG. 1 is a side view of the invention;

FIG. 2 is a front view of the present invention;

FIGS. 3-6 provide enlarged side, front, bottom and top views, respectively, of the blade portion of the invention; and FIG. 7 is a side view of the invention shown in the grasp of a user.

DETAILED DESCRIPTION OF A PREFERRED EMBODIMENT

Referring now to FIGS. 1 and 2, it will be seen that the instrument of the present invention 10 comprises an elongated cylindrical structure having a blade 12, a shaft 14, and an S-shaped handle 16. In a preferred embodiment of the invention, the instrument is made of 1008 carbon steel wire of approximately 7½ inches in length and about 4 millimeters in diameter. During the manufacturing process this 7½ inch straight wire is formed in an air bender to create the S-shaped curved handle 16 and the other end is stamped in a punch press as a first step of forming the blade portion 12. As seen in FIGS. 3-6 which provide enlarged views of the blade portion 12, the blade of the present invention comprises three surfaces 18, 20 and 22. Blade surface 18 is formed by punch press stamping the end of the tool 10 approximately eight millimeters from the tip while blade surfaces 20 and 22 are formed by grinding. Surface 20 is ground to an angle of approximately 10 degrees with respect to the longitudinal axis of shaft 14 and surface 22 is ground to an angle of approximately 50 degrees with respect to that axis. These two ground planar surfaces 20 and 22 intersect along a cutting edge line 24 which forms the principal working edge of the instrument.

The contemplated manner for holding the instrument in use is illustrated in FIG. 10 wherein it is seen that a predominant portion of the S-shaped handle 16 resides in the user's palm with the user's thumb and forefingers grasping shaft 14 at a comfortable distance from the blade 12.

It will now be understood that what has been disclosed herein comprises a simple and low cost but highly advantageous grinding instrument that finds particular application in use by denture wearers for emergency home care adjustment of their dentures. A preferred embodiment of the invention has been disclosed and comprises a carbon steel wire formed to provide an S-shaped handle and an elongated shaft terminating in a blade having a sharp cutting or grinding edge. However, it will also be understood that the invention is not to be limited by way of such use and may find other highly advantageous applications such as carving and scraping wood and other materials. Those having skill in the art to which the present invention pertains will, as a result of applicant's teaching herein, now perceive of various modifications that may be made to the invention such as changes in material and shape to provide a tool of comparable simplicity and ease of manufacture. However, it will be understood that such modifications are contemplated as being within the scope of the present invention which is to be limited only by the claims appended hereto.

I claim:

1. A denture grinding instrument for use in one hand and comprising a unitary elongated cylindrical wire having about one-half of its length formed into an S-shaped handle portion and the remaining length formed into a substantially straight shaft terminating in the angular surfaced blade, said S-shaped handle portion being angled relative to said shaft whereby to permit grasping of said shaft between the thumb and forefingers with the palm bearing against said handle portion.

* * * * *